United States Patent
Stein et al.

(10) Patent No.: US 6,329,153 B1
(45) Date of Patent: Dec. 11, 2001

(54) METHOD FOR EVALUATING IMMUNOSUPPRESSIVE REGIMENS

(75) Inventors: Charles M. Stein, Nashville; John J. Murray; Alastair J. J. Wood, both of Brentwood, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/337,967

(22) Filed: Jun. 22, 1999

Related U.S. Application Data (60) Provisional application No. 60/090,272, filed on Jun. 22, 1998, now abandoned.

(51) Int. Cl.[7] .................................................. G01N 33/53
(52) U.S. Cl. .......................... 435/7.1; 435/7.2; 435/7.92; 435/355; 435/372; 435/366; 436/512; 530/351
(58) Field of Search .......................... 435/7.1, 7.2, 7.92, 435/355, 372, 366; 436/512; 530/351

(56) References Cited

PUBLICATIONS

Van Den Berg et al. Transplantation, vol. 65, No. 8, pp. 1066–1071, Apr. 1998.*
Koutouby et al. Human Immunology. vol. 36, pp. 227–234, 1993.*
Frieling et al. Antimicrobial Agents and Chemotherapy. vol. 41, No. 7, pp. 1439–1443, Jul. 1997.*

* cited by examiner

Primary Examiner—Christine J. Saoud
Assistant Examiner—Fozia Hamud
(74) Attorney, Agent, or Firm—Benjamin Aaron Adler (57) ABSTRACT

The present invention describes a simple technique that provides a biologically relevant measure of the inhibitory effect of cyclosporine in vivo. This ability to measure response to cyclosporine may improve prediction of the efficacy of immunosuppressive treatment in patients and may allow optimal immunosuppression in individual patients.

9 Claims, 5 Drawing Sheets

METHOD FOR EVALUATING IMMUNOSUPPRESSIVE REGIMENS

CROSS-REFERENCE TO RELATED APPLICATION

This patent application claims benefit of provisional patent application U.S. Ser. No. 60/090,272, filed Jun. 22, 1998, now abandoned.

FEDERAL FUNDING LEGEND

This invention was produced in part using funds obtained through GM 5M01-RR00095 from the National Institute of Health. Consequently, the federal government has certain rights in this invention.

BACKGROUND OF THE INVENTION

1. Field of the Invention

The present invention relates generally to immunosuppression and the use of cyclosporin. More specifically, the present invention relates to a method of evaluating an immunosuppressive regimen on a patient-by-patient basis.

2. Description of the Related Art

The addition of cyclosporine (CSA) to the immunosuppressive regimens following organ transplantation has resulted in a marked improvement in graft survival (1,2). Cyclosporine, which remains an important component of most anti-rejection immunosuppressive regimens is, however, a problematic drug to use. The optimal clinical use of cyclosporine aims to both maximize efficacy, thus maintaining graft survival and to minimize drug-related toxicity.

Optimal clinical use has remained controversial, not only because of a poorly defined relationship between the dose of cyclosporine administered and the concentration of cyclosporine achieved, but also because both cyclosporine dose and concentration are poor predictors of clinical efficacy and toxicity (3-6). Thus, as detailed in recent reviews (4-6), numerous studies have examined the relationship between clinical efficacy and various pharmacokinetic parameters of cyclosporine disposition, such as trough concentrations, area-under-the-concentration-time curve (AUC), average cyclosporine concentrations and clearance. Some studies have shown a relationship between each of these pharmacokinetic measures and efficacy, but the correlation between any measure of cyclosporine disposition and efficacy is poor. This is reflected by a wide range of clinical practice, as demonstrated in the most recent consensus guidelines on the monitoring of cyclosporine concentrations after organ transplantation, where a wide range of cyclosporine trough concentrations was designated as "therapeutic" by different institutions (7).

The pharmacokinetics of cyclosporine are highly variable, both between patients and within the same patient (3). Even with the new microemulsion preparation of cyclosporine, which has less inter-individual and intra-individual pharmacokinetic variability than the older formulation pharmacokinetic characteristics, cyclosporine may vary 2-3 fold among individuals and 1-2 fold in the same individual (8-10). This pharmacokinetic variability has resulted in much of the effort being focused on the measurement of drug concentrations, and subsequent manipulation of dose, in order to achieve target cyclosporine concentrations within a poorly defined "therapeutic range" (11). However, it has long been noted that clinical response, with regard to both efficacy and drug-related toxicity, may be different in patients with similar concentrations of cyclosporine (5,12). This suggests that, in addition to interindividual pharmacokinetic differences in drug disposition, interindividual pharmacodynamic differences in response to drug may contribute to the weak relationship between concentrations of cyclosporine and clinical response.

The immunosuppressive action of cyclosporine may be mediated largely through effects on lymphocytes. After intracellular binding to cyclophilin, the cyclosporine-cyclophilin complex binds and inhibits the action of calcineurin, thereby reducing nuclear translocation of the cytoplasmic subunit of the nuclear factor of activated T-cells to the nuclear subunit, resulting in decreased T-cell receptor transcription of the interleukin-2 (IL-2) gene (13,22). Inhibition of IL-2 production is thought to be critical to the immunosuppressive effect of cyclosporine (13) and the inhibitory effect of cyclosporine on lymphocyte proliferation can be reversed by the addition of exogenous IL-2 (13). Further evidence for the immunological importance of inhibition of IL-2 production is provided by recent studies showing that blockage with monoclonal antibodies of the IL-2 receptor reduced the frequency of transplant rejection (23).

The inhibition of mitogen stimulated IL-2 in isolated peripheral blood lymphocytes by cyclosporine has been studied as a potential pharmacodynamic measure of the effect of cyclosporine (18,24,25). Such studies have generally shown that IL-2 production is inhibited 35–40% in patients receiving cyclosporine (18). However, the cumbersome technique, which required isolation of lymphocytes, culture with mitogen for 48 hours and measurement of IL-2 by bioassay, as well as the highly variable interindividual responses and the lack of a well-defined association with cyclosporine concentrations achieved in vivo, have limited the practical application of this technique. Nevertheless, the potential importance of using IL-2 inhibition as a marker of the effect of cyclosporine was demonstrated by the observation that failure to inhibit IL-2 production was associated with an increased likelihood of organ rejection (16). These studies therefore suggested that a more refined measurement of cyclosporine-induced inhibition of IL-2 production might define a biologically relevant effect that would thus allow development of a pharmacodynamic measure to determine interindividual variability in response to cyclosporine.

The inhibitory effect of cyclosporine on interleukin-2 (IL-2) production is thought to be critical to its immunosuppressive action (13). Several investigators have attempted to use the inhibitory effect of cyclosporine on IL-2 production, or on IL-2-dependent lymphocyte proliferation, as pharmacodynamic measures of response to cyclosporine (14–18). However, these techniques have been problematic. Plasma concentrations of IL-2 in humans are low, and it is therefore not practical to reliably detect a cyclosporine-induced, concentration-dependent, decrement of plasma IL-2 concentrations (14). Studies have thus examined either the effect of plasma from patients receiving cyclosporine on the proliferation of normal third party lymphocytes, or have otherwise isolated lymphocytes from patients who have received cyclosporine and examined the ability of these isolated lymphocytes to proliferate in culture or to produce IL-2 after mitogen stimulation.

Plasma obtained from patients receiving cyclosporine is not ideal for determining a pharmacodynamic response since approximately 50–70% of the drug is concentrated in erythrocytes in a temperature-dependent fashion (5,19). Thus, plasma cyclosporine concentrations are much lower than whole blood cyclosporine concentrations, and are critically dependent on the temperature at which the plasma is separated from blood. Plasma is therefore an unsuitable matrix for the measurement of both the pharmacokinetic and pharmacodynamic characteristics of cyclosporine. For these reasons, determination of cyclosporine concentrations in patients for therapeutic monitoring is now almost exclusively performed in whole blood samples rather than in plasma (7).

The alternative strategy of using isolated lymphocytes in culture (ex vivo) to measure a pharmacodynamic effect of cyclosporine is also problematic. First, the isolation of lymphocytes from blood separates these lymphocytes from the complex, cyclosporine-rich milieu in which their pharmacodynamic response occurs. This may alter both the response and rate of recovery (20). Second, isolation of lymphocytes involves multiple washes, which are likely to variably deplete cyclosporine concentration within the isolated lymphocytes. Third, the requirement of lymphocytic cell culture for 48 hours or longer limits the practical application of any pharmacodynamic measure obtained using such techniques.

The lack of a biologically relevant, practical pharmacodynamic measure of the effect of cyclosporine has been a significant obstacle to defining interindividual variability in response to cyclosporine, and development of such a measure has remained an elusive goal (4,5). Thus, the prior art is deficient in a method to evaluate the biological effects of drugs such as cyclosporine for individual patients, i.e., an evaluation which would provide more information than mere measurement of drug concentration. The present invention fulfills this long-standing need and desire in the art.

SUMMARY OF THE INVENTION

Herein is described a simple pharmacodynamic measure of the effect of cyclosporine determined in whole blood, both in vitro and ex vivo, and its relationship to cyclosporine concentrations that demonstrates marked interindividual variability in response to cyclosporine. The present invention demonstrates first, that the inhibition of stimulated IL-2 production in whole blood by cyclosporine, both in vitro and ex vivo, is related to the concentration of cyclosporine; second, that after the administration of oral cyclosporine, the IL-2 inhibitory response has a rapid onset and then declines rapidly as concentrations of cyclosporine fall; and third, that there is considerable interindividual variability in IL-2 inhibition in response to similar concentrations of cyclosporine.

One object of the present invention is to optimize the effects of treatment with an immunosuppressive agent, by measuring the effects of such agents on the inhibition of cytokine production in the blood of individuals receiving treatment.

In one embodiment of the present invention, there is provided a method of measuring the biological effect of treatment with an immunosuppressive or immunomodulatory agent in an individual, comprising the steps of: extracting a blood sample from said individual; treating the blood sample with a mitogenic agent; measuring the concentration of cytokines in the blood sample; and comparing the concentration of cytokines prior to and after the treatment with said immunosuppressive or immunomodulatory agent, wherein treatment with the agent resulting in an inhibition of said cytokines reflects a biological effect. The sample may be treated with a mitogenic agent for about 1 hour to about 6 hours, and sample may be plasma, serum and whole blood. Representative examples of the agent include cyclosporin, cyclosporin A, tacrolimus, rapamycin, leflunomide, glucocorticoids, mycophenolate mofetil as well as biological agents such as tumor necrosis factor antibodies, interleukin-2 receptor antibodies, interleukin-1 receptor antibodies, other anti-cytokine or antilymphocyte antibodies and azathioprine. Representative examples of the mitogenic agent include phytohemmagluttinin, phorbol esters, lipopolysaccharides an d calcium ionophores. Preferably, the cytokines measured are interleukin-2, tumor necrosis factor alpha and beta, interleukin-1 and interferon-gamma.

In another embodiment of the present invention, the above-described method may be used to treat individuals who have received a medical procedure such as an organ or cell transplant or a tissue graft, or in such cases as when the individual suffers from a disease such as an auto-immune disease or anti-inflammatory disease. The purpose of the above-described treatment is to prevent or treat transplant or graft rejection; to prevent or treat toxicity to said immunosuppressive agent; or to maintain the therapeutic effect of said immunosuppressive agent within a target range. This target range is defined as approximately midway between a peak and a trough biological effect of the immunosuppressive agent.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Interindividual variability in response to cyclosporine is thought to contribute to differences in clinical outcome. The lack of a pharmacodynamic measurement of the effect of cyclosporine has been a significant obstacle to defining interindividual variability in response to cyclosporine. The invention described herein discloses a practical, biologically relevant pharmacodynamic measurement of the effect of cyclosporine that allows determination of interindividual variability in response to cyclosporine.

The inhibition of phytohemagglutinin (PHA)-stimulated IL-2 production by cyclosporine was measured by ELISA in whole blood. Ex vivo studies were performed on blood drawn before, 4 an d 24 hours after subjects received 4 mg/kg cyclosporine orally (n=18). To further define the onset of inhibition of IL-2 production b y cyclosporine, subjects (n=5) were studied at intervals over 240 minutes after oral administration of cyclosporine (n=5). To determine the in vitro concentration-response curve, the effect of 0–1200 ng/ml cyclosporine on IL-2 inhibition was determined in whole blood (n=4).

Four hours after administration of cyclosporine, the mean (±SEM) cyclosporine concentration was 702±46 ng/ml and PHA-stimulated production of IL-2 was significantly decreased from a baseline value of 1790±173 pg/ml to 555±81 pg/ml (68.7±4.0% inhibition) ($P<0.0001$) (n=18). Twenty four hours after cyclosporine administration, although cyclosporine was still present in low concentrations (64±6 ng/ml), IL-2 production was not inhibited and was slightly greater than baseline (6.1±7.0%). A rapid, concentration-dependent, inhibitory effect of cyclosporine on stimulated IL-2 production was observed after subjects received cyclosporine. Maximum cyclosporine concentrations at 90 and 120 minutes (944±83 ng/ml and 953±84 ng/ml, respectively) were accompanied by maximum inhibition of IL-2 production (87% ±1% and 84% ±2%, respectively) (n=5).

The inhibitory effect of cyclosporine on IL-2 production decreased as cyclosporine concentrations fell. In vitro cyclosporine at concentrations ranging from 32.5–1200 ng/ml inhibited the production of IL-2 in a dose dependent fashion with an $IC_{50}$ of approximately 300 ng/ml. These results were similar for both the in vitro and ex vivo responses. These data suggest that the concentration-response curve for cyclosporine is steep, with considerable inter-individual variability. Inhibition of stimulated IL-2 production in whole blood by cyclosporine provides a simple measure of drug effect that will allow variability in response to cyclosporine to be measured in patients receiving cyclosporine, and thus allow individualization of immunosuppressive regimens.

The present invention is directed towards a method of evaluating individual patients to determine the immunosuppressive effects of cyclosporine, thereby allowing patient-specific, optimized regimens to be developed.

In accordance with the present invention, there may b e employed conventional molecular biology, microbiology, immunology and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D.N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, the term "therapeutic effect" is defined as modulation of the immune system so as to prevent rejection of a transplanted organ or graft or so as to treat the manifestation of autoimmune disease or inflammation.

As used herein, the terms "peak biological effect" and "trough biological effect" are defined as maximum (80–100 i.) and minimum (0.1) inhibition of cytokine production.

As used herein, the term "peak concentration" and "trough concentration" are defined as the maximum concentration of drug in blood or tissue after administration of the drug and the lowest concentration of drug before the next dose (usually 12 or 24 hours after the previous dose).

The following examples are given for the purpose of illustrating various embodiments of the invention and are not meant to limit the present invention in any fashion:

EXAMPLE 1

Materials And Assays

Cyclosporin A and phytohemagglutinin-P (PHA) were obtained from Sigma Chemicals (St. Louis, Mo.). Human IL-2 immunoassay kits were obtained from R&D Systems (Minneapolis, Minn.). Cyclosporine (1 mM) was dissolved in dimethylsulfoxide and subsequently diluted in sterile normal saline to a final working concentration of 10 $\mu$M immediately before use. PHA was diluted to a concentration of 1 mg/ml in sterile normal saline and frozen in aliquots that were thawed immediately before use.

IL-2 concentrations were determined by ELISA (R&D Systems Minneapolis, Minn.). The lower limit of IL-2 detection was 31.2 pg/ml. Cyclosporine concentrations in whole blood were determined using fluorescence polarization immunoassay (FPIA) (Abbott Diagnostics Inc, Abbott Park, Ill.).

EXAMPLE 2

Experimental Protocol

All subjects provided written informed consent, and the study protocol was approved by the Vanderbilt Committee for the Protection of Human Subjects. Subjects were healthy, normotensive, non-smoking, male volunteers. No subject had clinically significant abnormalities upon history, physical examination or routine laboratory tests, including complete blood count, prothrombin and partial thromboplastin times, renal and liver function tests and electrocardiogram. Subjects did not take any medications for at least two weeks before each study day and abstained from caffeine and alcohol for 5 days before each study day. Subjects fasted overnight before each study day. All experiments were performed in the Vanderbilt Clinical Research Center with the subjects resting supine in bed. An intravenous canula was placed in an antecubital vein. Thirty minutes later, baseline venous blood samples were drawn and cyclosporine (4 mg/kg) was administered by mouth with 150 ml water. Subjects remained fasting for 5 hours after the administration of cyclosporineand were then fed a standardized lunch. Venous blood (5 ml) was drawn into an EDTA tube for determination of cyclosporine concentrations and into a heparinized tube for measurement of PHA-stimulated IL-2 concentrations at the intervals indicated in each substudy.

EXAMPLE 3

Ex Vivo Study 1

To determine the relationship of the IL-2 inhibitory response to peak and trough cyclosporine concentrations, venous blood was drawn from 18 subjects before, and 4 and 24 hours after the administration of 4 mg/kg cyclosporine (Neoral, Novartis N.J.). Cyclosporine concentrations and PHA-stimulated IL-2 production were measured. The preliminary studies that defined the optimum conditions for the measurement of cytokine production in whole blood have been previously described (21). Duplicate samples (in 1 ml total volume) of whole blood (950 µl) and 50 µg/50 µl PHA (stimulated) or 50 µl saline (unstimulated) were incubated for 6 hours at 37° C. in a shaking water bath. At the end of the incubation, the samples were centrifuged in an Eppendorf microfuge for 2 minutes and the supernatant removed and stored at −70° C. until assayed. Because the coefficient of variation in duplicate incubations was small (11.4% ±1.3%), in subsequent studies, single sample incubations were performed. PHA-stimulated IL-2 production determined in blood obtained from each subject immediately before the administration of cyclosporine represented the baseline response in that individual (0% inhibition). Subsequent IL-2 production in samples obtained after cyclosporine administration was expressed relative to the baseline IL-2 production.

EXAMPLE 4
Ex Vivo Study 2

After Study 1 showed a rapid onset of IL-2 inhibition within 4 hours of the administration of cyclosporine and complete recovery within 24 hours, the onset of the response and its relationship to cyclosporine concentrations were further defined as follows. Venous blood was sampled from 5 subjects before and 30, 60, 90, 120, 180 and 240 minutes after the administration of 4 mg/kg cyclosporine (Sandimmune, Novartis, N.J.) and cyclosporine concentrations and PHA-stimulated IL-2 production were measured. The Sandimmune formulation of cyclosporine was used because it results in lower blood cyclosporine concentrations than the Neoral preparation, and therefore, by combining the data from Studies 1 and 2, would allow examination of the effects of cyclosporine over a wider range of concentrations.

EXAMPLE 5
In Vitro Study 3

Venous blood was drawn from 4 healthy volunteers into heparinized tubes, maintained at 37° C. and used within 60 minutes. To measure the inhibition of IL-2 production by cyclosporine in vitro, 50 µg/50 µl PHA and cyclosporine, in final concentrations ranging from 0–1 µM (0–1200 ng/ml), were incubated with whole blood for 6 hours in a total volume of 1 ml (850 µl blood, 50 µl PHA and 100 µl cyclosporine) at 37° C. in a shaking water bath. At the end of the incubation, the samples were centrifuged in an Eppendorf microfuge for 2 minutes and the supernatant removed and stored at −70° C. until assayed.

EXAMPLE 6
Data Analysis

Data are expressed throughout as mean ±SEM. The decrement of IL-2 production in PHA-stimulated whole blood obtained from subjects after administration of cyclosporine and in samples incubated with cyclosporine in vitro was expressed as percent inhibition relative to the baseline PHA-stimulated IL-2 response determined in the absence of cyclosporine. Dose-response curves were analyzed with a sigmoid $E_{max}$ model (Fig Perfect, Biosoft) and the concentration of cyclosporine resulting in 50% of the maximal inhibitory response ($IC_{50}$) determined. Data that were normally distributed were analyzed by repeated measure analysis of variance and the t-test for paired or unpaired samples as appropriate. Comparison of data that were not normally distributed were performed using a Wilcoxon matched pairs signed rank test or a Mann-Whitney U test as appropriate (SPSS for Windows Release 6, SPSS, Chicago). A two-tailed P value of less than 0.05 was the criterion for statistical significance.

EXAMPLE 7
Results From Study 1

Figure 1:
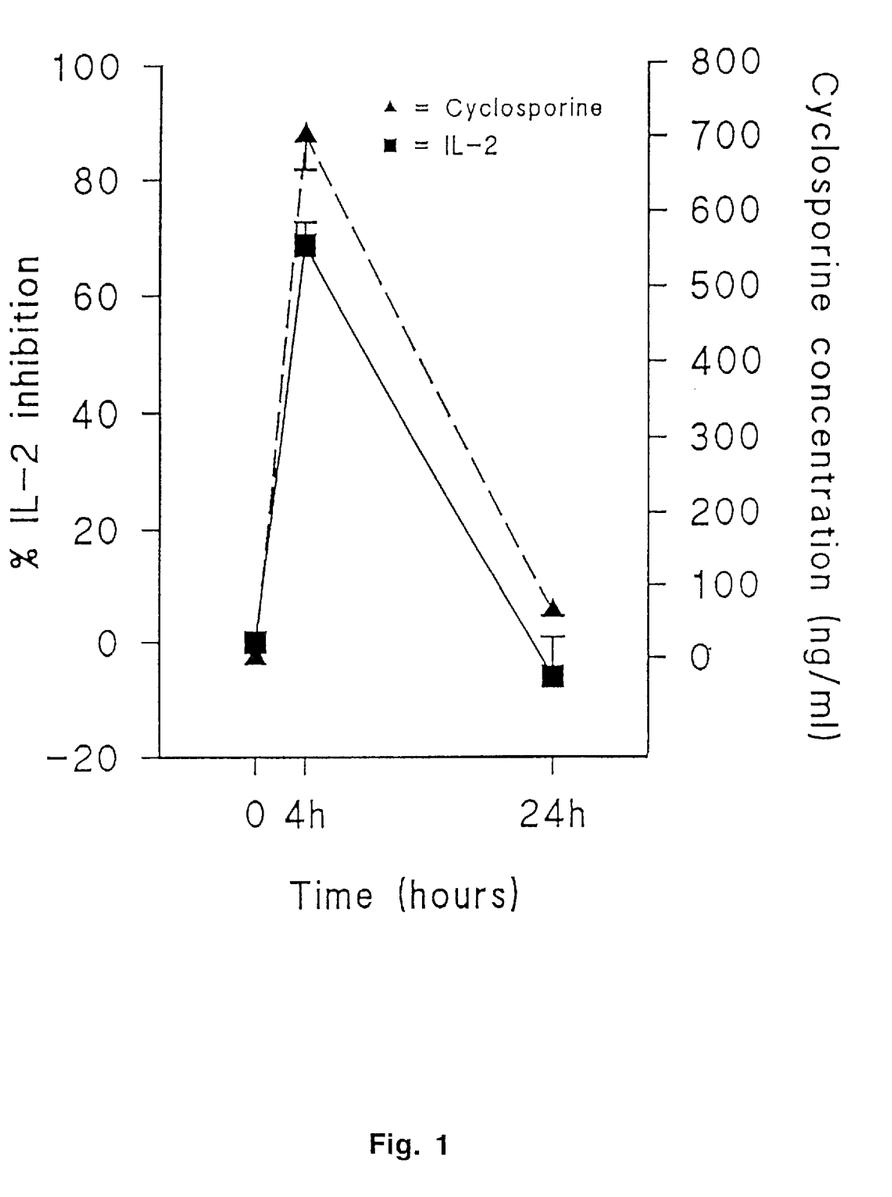
FIG. 1 shows the IL-2 inhibition (square) and blood concentrations of cyclosporine (triangle) (mean±SEM) 4 hours (n=18) and 24 hours (n=15) after oral administration of 4 mg/kg cyclosporine.

IL-2 concentrations in unstimulated whole blood incubated for 6 hours were below 32.1 pg/ml, the lower limit of detection for the assay. Ex vivo PHA stimulation of whole blood drawn at baseline, before subjects received cyclosporine, resulted in a mean IL-2 concentration of 1790±173 pg/ml (n=18). In the blood samples drawn 4 hours after subjects had received cyclosporine, the mean cyclosporine concentration was 702±46 ng/ml, and PHA-stimulated production of IL-2 was significantly decreased to 555±81 pg/ml (68.7±4.0% inhibition) (P<0.0001) (FIG. 1). For technical reasons, IL-2 production was not measured in the 24 hour timepoint samples in 3 subjects. The average PHA-stimulated IL-2 production in the remaining 15 subjects was 2027±221 pg/ml in blood drawn 24 hours after cyclosporine administration, at which time the average cyclosporine concentration was 64±6 ng/ml. IL-2 production was not inhibited 24 hours after subjects had received cyclosporine, and was 6.1±7.0% greater than the IL-2 production before cyclosporine administration (P=NS) (FIG. 1).

Blood from one subject produced 15-fold more IL-2 (estimated concentration of 33000 pg/ml) after PHA stimulation than was observed in any of the other 18 subjects whose mean stimulated IL-2 production was 1790±173 pg/ml. These data, while unexplained, are unlikely to be artefactual, since the same subject also performed Study 2 and again exhibited a similar magnified response. The IL-2 concentrations after PHA stimulation in this subject are far beyond the demonstrated linear range of the assay (2000 pg/ml), and although the IL-2 response was inhibited 49% 4 hours after cyclosporine administration, his data have not been included in the analysis.

EXAMPLE 8
Results From Study 2

Figure 2:
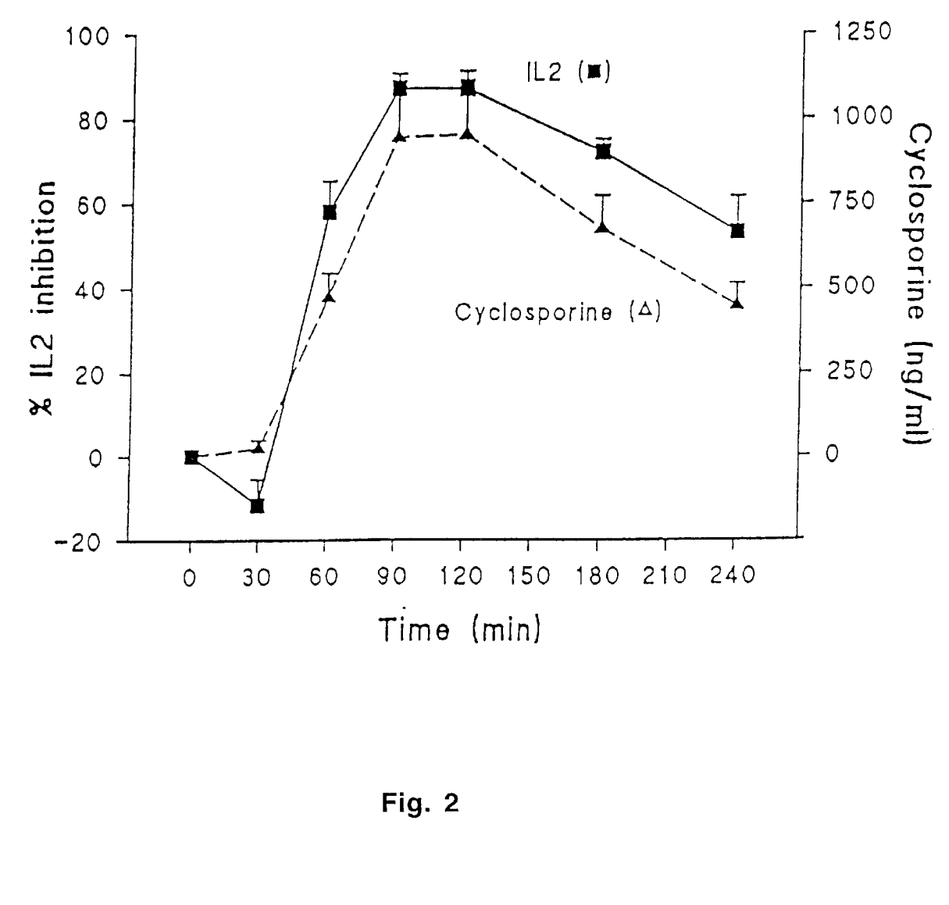
FIG. 2 shows a time course (30–240 minutes) of IL-2 (square) inhibition and blood concentrations of cyclosporine (triangle) (mean±SEM) after oral administration of 4 mg/kg cyclosporine (n=5).

The timecourse of the inhibition of IL-2 production by cyclosporine and its relationship to the blood concentrations of cyclosporine 30–240 minutes after the administration of 4 mg/kg cyclosporine is shown in FIG. 2. A rapid, concentration-dependent, inhibitory effect of cyclosporine on stimulated IL-2 production was observed. Maximum cyclosporine concentrations occurred 90 and 120 minutes after the administration of cyclosporine (944±83 ng/ml and 953±84 ng/ml, respectively). Similarly, maximum inhibition of IL-2 production was also observed 90 and 120 minutes after the administration of cyclosporine (87% ±1% and 84% ±2%, respectively) (FIG. 2). The inhibitory effect of cyclosporine on IL-2 production decreased as cyclosporine concentrations fell. Four hours after the administration of drug, the mean cyclosporine concentration was 446±30 ng/ml and the mean inhibition of IL-2 production was 53% ±8%.

EXAMPLE 9
Results From Study 3

Figure 3:
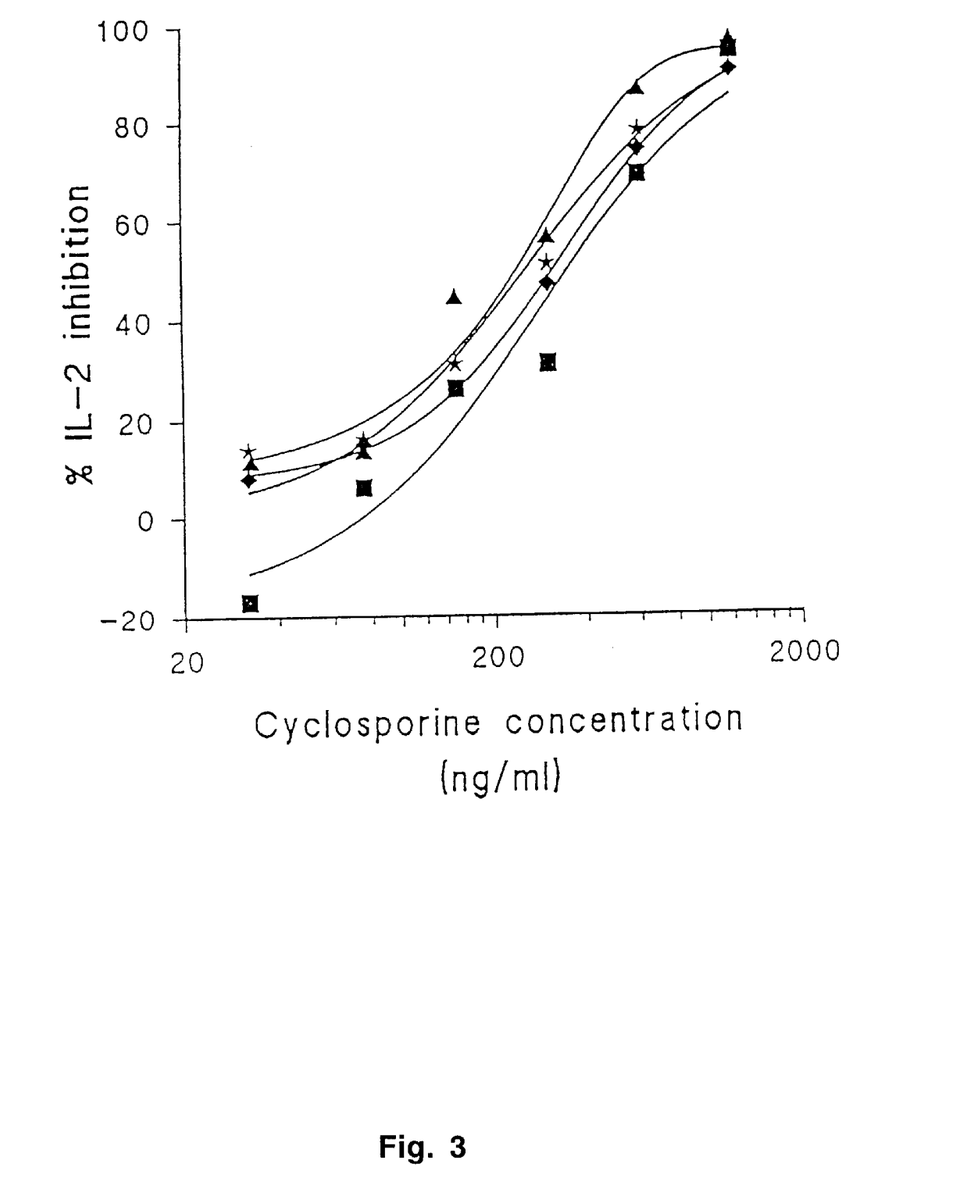
FIG. 3 shows in vitro inhibition of IL-2 production by cyclosporine (32.5–1200 ng/ml) in whole blood in 4 subjects.

Cyclosporine, at concentrations ranging from 32.5–1200 ng/ml, inhibited the production of IL-2 in vitro in a dose-dependent fashion in all 4 subjects (FIG. 3). In the 4 individuals, the concentration of cyclosporine required to inhibit the maximal response by 50%, the $IC_{50}$, was 280, 233, 256, and 347 ng/ml.

Figure 4:
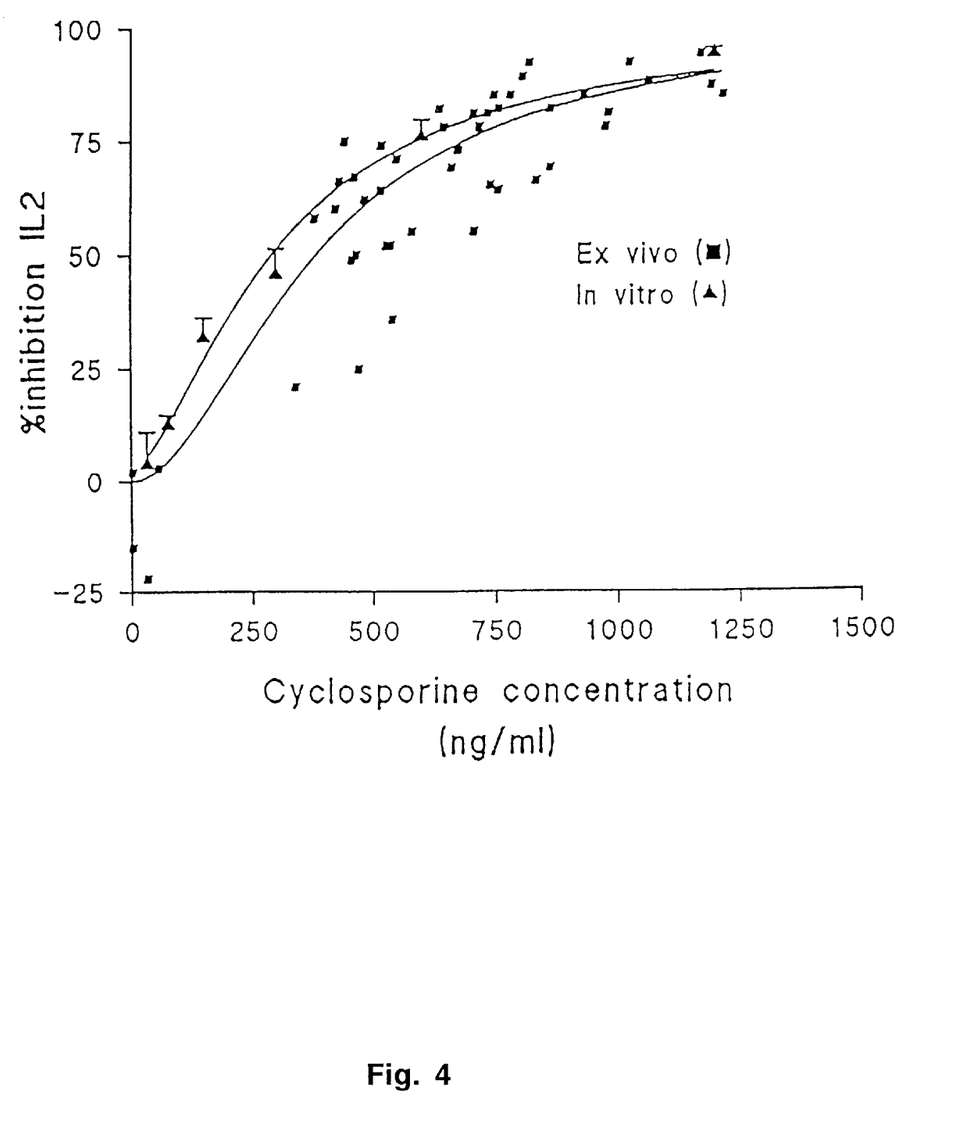
FIG. 4 shows the relationship between blood cyclosporine concentrations and IL-2 inhibition in 4 hour samples (Study 1) and 30–240 minute samples (Study 2) represented as individual points (square) and the in vitro IL-2 inhibition b y cyclosporine concentration-response curve (triangle) (Study 3) (n=4, mean±SEM).

The blood concentrations of cyclosporine studied in vitro spanned the range of blood cyclosporine concentrations achieved in vivo after the oral administration of cyclosporine in Studies 1 and 2. The relationship between blood cyclosporine concentrations and IL-2 inhibition in 4 hour samples (Study 1) and 30–240 minute samples (Study 2), with each timepoint represented as an individual point, is shown in FIG. 4. Superimposed is the solid line representing the mean (±SEM) in vitro IL-2 inhibition by cyclosporine as a concentration-response curve (Study 3). The sigmoid concentration-response relationship is evident in both the ex vivo and in vitro studies, as is the close relationship between the cyclosporine concentration-response curve determined in vitro and ex vivo.

Figure 5:
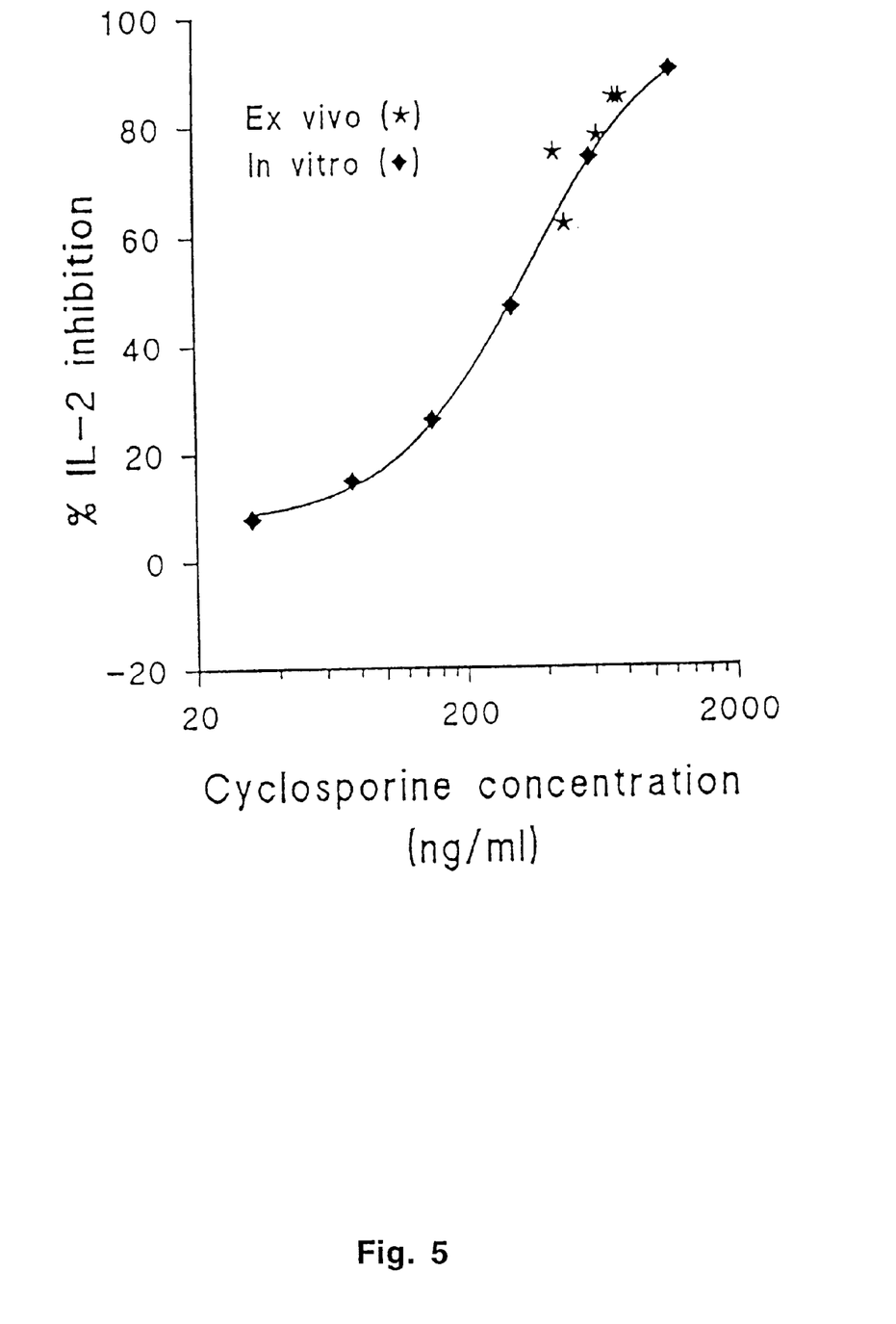
FIG. 5 shows in vitro IL-2 inhibition by cyclosporine (concentration-response curve) (diamond) in 1 subject and ex vivo inhibition of IL-2 in the same subject on the same day at various concentrations of cyclosporine after oral administration of 4 mg/kg cyclosporine (star).

In one subject, the in vitro cyclosporine concentration-response (Study 3) was determined in blood drawn immediately before the administration of 4 mg/kg cyclosporine for Study 2. FIG. 5 shows the excellent relationship between the in vitro IL-2 inhibition by cyclosporine (concentration-response curve) in this subject, and the ex vivo inhibition of IL-2 resulting from the various concentrations of cyclosporine that occurred after oral administration to the same subject on the same day.

EXAMPLE 10

Summary

These results offer several practical advantages and new insights over the prior art. The use of whole blood for IL-2 stimulation assays not only simplifies previous techniques, but also allows the pharmacodynamic effect of the actual concentration of cyclosporine present in the blood to be determined in th e environment in which the in vivo response will occur. This avoids the confounding effects introduced by the lymphocyte isolation procedures, which not only remove the lymphocytes from the cyclosporine-rich environment, but are likely to variably deplete intracellular concentrations of cyclosporine. The whole blood technique thus allows the measurement of both cyclosporine concentration and effect in the same matrix. This results in an ideal situation for defining the relationship between concentration and effect. The 6 hour incubation obviates the requirement for cell-culture facilities, and measurement of IL-2 concentrations by ELISA further simplifies the technique.

Study 1 examined the effects of cyclosporine 4 and 24 hours after drug administration. These timepoints were chosen to approximately coincide with peak and trough drug concentrations and to provide information regarding the onset and duration of cyclosporine action on IL-2 inhibition. In a previous study that used isolated lymphocytes, the onset of action of a pharmacodynamic response was thought to be delayed 4–12 hours after administration of cyclosporine (18). The present invention demonstrates that a marked effect on IL-2 inhibition was present 4 hours after cyclosporine had been administered to subjects and that this effect had completely reversed 24 hours after drug administration (although at that time, cyclosporine concentrations were still 64±6 ng/ml, a concentration of cyclosporine that would be expected from in vitro studies performed in lymphocytes to have biological effects (15)).

Study 2 further characterized the speed of onset of inhibition of IL-2 production by cyclosporine and its relationship to drug concentrations. The onset of effect of cyclosporine was found to occur rapidly, with peak inhibition of IL-2 production, approximately 85%, occurring 90 to 120 minutes after drug administration and coinciding with peak cyclosporine concentrations, which were approximately 950 ng/ml (FIG. 2). The inhibitory effect decreased rapidly, in concert with the concentration of cyclosporine, such that 4 hours after administration, when blood concentrations of cyclosporine had decreased to 446 ng/ml, the IL-2 response was only inhibited 53%. Comparing the inhibition of IL-2 4 hours after the administration of cyclosporine in Study 1 and Study 2, which used different formulations of cyclosporine, further demonstrates the concentration-related effect of cyclosporine on IL-2 inhibition. Thus, in Study 1, which used the more efficiently absorbed microemulsion formulation of cyclosporine, the concentration of cyclosporine 4 hours after administration was 702 ng/ml, which resulted in 69% inhibition of IL-2 production. This is in comparison to Study 2, where a cyclosporine concentration of 446 ng/ml resulted in 53% inhibition of IL-2 production 4 hours after administration of cyclosporine.

A small, but detectable apparent paradoxical increase in IL-2 production was noted in some subjects at low concentrations of cyclosporine, both in vitro and ex vivo (FIGS. 2 and 3). The mechanism underlying this observation is unclear, but it has previously been noted that in some patients, IL-2 production in isolated lymphocytes was paradoxically increased 12–16 hours after cyclosporine, a time when low concentrations of drug are likely to have been present (18).

The in vitro incubation of whole blood with increasing concentrations of cyclosporine resulted in a concentration-dependent inhibition of IL-2 production by cyclosporine, which was remarkably similar to the concentration-response observed ex vivo in whole bloodt of subjects who had received cyclosporine. Thus, from the fitted $E_{max}$ curves, the estimated concentration of cyclosporine required to inhibit maximal response 50% ex vivo (291 ng/ml) and in vitro (283 ng/ml) were very similar. This is further illustrated in FIG. 5, which shows a close relationship between the in vitro and ex vivo concentration-dependent inhibition of IL-2 by cyclosporine in one subject in whom both studies were performed on the same day.

The widespread clinical use of trough cyclosporine concentrations to optimize therapy in patients has developed empirically. Thus, trough levels above a particular value, the absolute value of which varies 2-3 fold according to the method used to measure cyclosporine concentrations and the matrix (blood or serum) in which it is measured, have been associated with improved graft survival in some studies, and have thus been designated a therapeutic target (4,5,7). The present studies suggest that IL-2 production is not inhibited at low concentrations of cyclosporine and may not in fact be significantly inhibited during much of the dose cycle in some patients. The inability of trough cyclosporine concentrations to reliably predict efficacy (6) may in part b e explained by the observations herein that the immunosuppressive activity of cyclosporine, as determined by inhibition of IL-2 production, may be low at trough concentrations, thus rendering a measurement of trough cyclosporine concentration a poor predictor of overall efficacy. Similarly, other studies which have attempted to improve the ability to predict efficacy on the basis of pharmacokinetic measures, have used a composite measure of cyclosporine disposition such as AUC or average cyclosporine concentrations. The results disclosed herein suggest that such composite measures of cyclosporine disposition, which potentially include many timepoints at which cyclosporine concentrations may not be associated with a significant immunosuppressive effect, as well as many timepoints at which the concentrations of cyclosporine are greater than that required for maximum effect, are unlikely to adequately predict immunosuppressive efficacy. Furthermore, these results demonstrate a scatter of pharmacodynamic responsiveness among individuals, with similar concentrations of cyclosporine resulting in a range of inhibition of IL-2. This provides another explanation for the limited ability of any pharmacokinetic measure to reliably predict immunosuppressive efficacy.

The present invention has shown that the cyclosporine concentration-response curve, as determined by IL-2 inhibition, is steep, with cyclosporine concentrations below 150 ng/ml having little effect, while those above 900 ng/ml result in little additional response. These findings suggest that it may be possible to define a therapeutic range of cyclosporine concentrations for individuals based on this pharmacodynamic measure of response. Wide fluctuations in cyclosporine concentrations may be counterproductive, resulting in little or no increased efficacy at concentrations above a certain threshold and limited efficacy at concentrations below a certain threshold. Thus, formulations of cyclosporine that result in a pharmacokinetic profile with minimal peak to trough fluctuations in drug concentration may allow more effective immunosuppression. Furthermore, the marked efficacy of current cyclosporine regimens in preventing organ rejection suggests that complete and continuous inhibition of IL-2 production is not required for clinical efficacy.

The following references were cited herein:
1. Burke, J. F. J., J. D. Pirsch, E. L. Ramos, D. R. Salomon, D. M. Stablein, B. Van, DH, and J. C. West. 1994. *New England J. of Med.* 331:358–363.
2. Anonymous. 1986. *New England J. of Med.* 314:1219–1225.
3. Fahr, A. 1993. *Clin. Pharmacokinetics* 24:472–495.
4. Sketris, I., R. Yatscoff, P. Keown, D. M. Canafax, M. R. First, D. W. Holt, T. J. Schroeder, and M. Wright. 1995. *Clin. Biochem.* 28:195–211.
5. Tsunoda, S. M. and F. T. Aweeka. 1996. *Clin. Pharmacokinetics* 30:107–140.
6. Lindholm, A. 1995. *Therapeutic Drug Monitoring* 17:631–637.
7. Oellerich, M., V. W. Armstrong, B. Kahan, L. Shaw, D. W. Holt, R. Yatscoff, A. Lindholm, P. Halloran, K Gallicano, and K Wonigeit. 1995. *Therapeutic Drug Monitoring* 17:642–654.
8. Wahlberg, J., H. E. Wilczek, P. Fauchald, K. P. Nordal, J. G. Heaf, K. Olgaard, J. M. Hansen, H. Lokkegaard, E. A. Mueller, and J. M. Kovarik. 1995. *Transplantation* 60:648–652.
9. Kovarik, J. M., E. A. Mueller, B. J. van, S. S. Fluckiger, H. Lange, Schmidt, W. H. Boesken, A. E. Lison, and K Kutz. 1994. *Transplantation* 58:658–663.
10. Kovarik, J. M., E. A. Mueller, B. J. van, W. Tetzloff, and K. Kutz. 1994. *J. of Phamn. Sci.* 83:444–446.
11. Friman, S. and L. Backman. 1996. *Clin. Pharmacokinetics* 30:181–193.
12. Kerman, R. H., P. M. Kimball, A. Lindholm, B. C. Van, S. M. Katz, R. M. Lewis, J. Podbielski, J. Williams, and B. D. Kahan. 1993. *Transplantation Proc.* 25:23–25.
13. Ho, S., N. Clipstone, L. Timmermann, J. Northrop, I. Graef, D. Fiorentino, J. Nourse, and GR. Crabtree. 1996. *Clin. Immun. & Immunopath.* 80:S40–S45
14. Awni, W. M. 1992. *Clin. Pharmacokinetics* 23:428–448.
15. Hirano T., Oka K, Takeuchi H., Kozaki K, Matsuno N., Nagao T., Kozaki M., Ichikawa M., Yoshida M., Umezawa Y., Hirata M., Ohi T., and Koga M. 1997. *Clin. Pharmac. & Therapeutics* 62:652–664.
16. Simpson, M. A., T. M. Young-Fadok, P. N. Madras, R. B. Freeman, R. A. Dempsey, D. Shaffer, D. Lewis, R. L. Jenkins, and A. P. Monaco. 1991. *Archives of Surgery* 126:717–719.
17. d'Uscio, C. H., F. T. Aweeka, T. Prueksaritanont, S. J. Tomlanovich, S. K. Gupta, M. V. Lantz, J. G. Gambertoglio, M. R. Garovoy, and L. Z. Benet. 1995. *J. of Clin. Phannac.* 35:967–973.
18. Yoshimura, N. and BD. Kahan. 1985. *Transplantation* 40:661–666.
19. Lensmeyer, G. L., D. A. Wiebe, and I. H. Carlson. 1989. *Clin. Chem.* 35:56–63.
20. Batiuk, T. D., F. Pazderka, J. Enns, L. DeCastro, and P. F. Halloran. 1995. *J. of Clin. Invest.* 96:1254–1260.
21. Murray, J. J., M. D. Mullins, H. R. Knapp, S. L. Keeler, W. E. Serafin, L. J. Roberts, B. J. Struthers, M. B. Grisham, and J. A. Oates. 1995. *Amer. J. of Therapeutics* 2:739–748.
22. O'Keefe, S. J., J. Tamura, R. L. Kincaid, M. J. Tocci, and E. A. O'Neill. 1992. *Nature* 357:692–694.
23. Vincenti F., Kirkman R., Light S., Bumgardner G., Pescovitz M., Halloran P., Neylan J., Wilkinson A., Ekberg H., Gaston R., Backman L., Burdick J., and for the Daclizumab Triple Therapy Study Group. 1998. *New England J. of Med.* 338:161–165.
24. Guillou, P. J., G. R. Giles, and C. W. Ramsden. 1986. *J. of Clin. Immun.* 6:373–380.
25. McKenna, R. M., D. N. Rush, P. Bakkestad-Legare, and J. R. Jeffery. 1988. *Transplantation* 45:76–81.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of measuring the biological effect of treatment with an immunosuppressive or immunomodulatory agent in an individual, comprising the steps of: extracting a sample of whole blood from said individual; treating the blood sample with a mitogenic agent for about 1 hour to about 6 hours, measuring the concentration of interleukin-2 (IL-2) in said blood sample; and comparing said concentration of IL-2 prior to and after said treatment with said immunosuppressive or immunomodulatory agent, wherein said treatment with said immunosuppressive agent resulting in an inhibition of IL-2 reflects a biological effect.

2. The method of claim 1, wherein said immunosuppressive or immunomodulatory agent is selected from the group consisting of cyclosporin, and immunomodulatory agents with similar mechanism of action as cyclosporin.

3. The method of claim 1, wherein said mitogenic agent is selected from the group consisting of phytohemmagluttinin, phorbol esters, lipopolysaccharides and calcium ionophores.

4. The method of claim 1, wherein said individual has received a medical procedure selected from the group consisting of an organ transplant, a cell transplant and a tissue graft.

5. The method of claim 1, wherein said individual has a disease selected from the group consisting of an autoimmune disease and inflammatory disease.

6. The method of claim 1, wherein the purpose of said treatment is to prevent or treat transplant or graft rejection.

7. The method of claim 1, wherein the purpose of measuring said biological effect is to prevent or treat toxicity to said immunosuppressive agent.

8. The method of claim 1, wherein the purpose of measuring said biological effect is to maintain the therapeutic effect of said immunosuppressive agent within a target range.

9. The method of claim 8, wherein said target range is approximately midway between a peak and a trough biological effect of said agent.

* * * * *